(12) United States Patent
Broussard

(10) Patent No.: US 9,808,492 B2
(45) Date of Patent: Nov. 7, 2017

(54) METHODS OF PREPARING LYOPHILIZED HUMAN TISSUES

(71) Applicant: Terry W. Broussard, The Woodlands, TX (US)

(72) Inventor: Terry W. Broussard, The Woodlands, TX (US)

(*) Notice: Subject to any disclaimer, the term of this patent is extended or adjusted under 35 U.S.C. 154(b) by 0 days.

(21) Appl. No.: 14/801,747

(22) Filed: Jul. 16, 2015

(65) Prior Publication Data

US 2015/0320906 A1 Nov. 12, 2015

Related U.S. Application Data

(63) Continuation of application No. 13/608,475, filed on Sep. 10, 2012, now abandoned.

(51) Int. Cl.

| *A61L 27/36* | (2006.01) |
| *A61K 35/50* | (2015.01) |
| *A61L 27/50* | (2006.01) |
| *A61L 27/60* | (2006.01) |
| *C12N 5/073* | (2010.01) |

(52) U.S. Cl.
CPC .......... *A61K 35/50* (2013.01); *A61L 27/3604* (2013.01); *A61L 27/3641* (2013.01); *A61L 27/3662* (2013.01); *A61L 27/3679* (2013.01); *A61L 27/3691* (2013.01); *A61L 27/507* (2013.01); *A61L 27/60* (2013.01); *C12N 5/0605* (2013.01); *A61L 2430/10* (2013.01); *A61L 2430/34* (2013.01)

(58) Field of Classification Search
CPC .................................................. A61L 2430/10
See application file for complete search history.

(56) References Cited

U.S. PATENT DOCUMENTS

| 8,357,403 B2 | 1/2013 | Daniel et al. |
| 8,372,437 B2 | 2/2013 | Daniel |
| 8,409,626 B2 | 4/2013 | Daniel et al. |
| 8,460,715 B2 | 6/2013 | Daniel |
| 8,460,716 B2 | 6/2013 | Daniel |
| 8,597,687 B2 | 12/2013 | Daniel |
| 8,623,421 B2 | 1/2014 | Daniel |
| 8,703,206 B2 | 4/2014 | Daniel et al. |
| 8,709,493 B2 | 4/2014 | Daniel et al. |
| 8,709,494 B2 | 4/2014 | Daniel |
| 8,932,643 B2 | 1/2015 | Daniel et al. |
| 8,940,684 B2 | 1/2015 | Koob |
| 8,946,163 B2 | 2/2015 | Koob |
| 8,986,378 B2 | 3/2015 | Koob |
| 9,005,285 B2 | 4/2015 | Niu et al. |
| 9,078,775 B2 | 7/2015 | Li et al. |
| 9,084,767 B2 | 7/2015 | Daniel et al. |
| 9,125,759 B2 | 9/2015 | Greenhalgh et al. |
| 9,155,799 B2 | 10/2015 | Koob |
| 9,179,976 B2 | 11/2015 | Paulos et al. |
| 9,180,145 B2 | 11/2015 | Brown et al. |
| 9,186,382 B2 | 11/2015 | Daniel et al. |
| 9,265,800 B2 | 2/2016 | Daniel |
| 9,265,801 B2 | 2/2016 | Daniel |
| 9,272,005 B2 | 3/2016 | Daniel |
| 9,433,647 B2 | 9/2016 | Daniel |
| 9,463,206 B2 | 10/2016 | Koob et al. |
| 9,463,207 B2 | 10/2016 | Daniel |
| 9,572,839 B2 | 2/2017 | Daniel |

OTHER PUBLICATIONS

Gajiwala et al. Cell and Tissue Banking, 2004, 5:73-80.*
Tyszkiewicz et al. Annals of Transplantation, 4(3-4):85-90.*
WebMD, LLC., "Are There Other Injectable Wrinkle Fillers?" Wrinkle Fillers, 2009, 2 pg., Available from: http://www.webmed.com/beauty/facial-fillers/cosmetic-procedures-collagen.
"FDA Approves Treatment IDE for Dermagraft(R)", PRNewswire, Advanced Tissues Sciences, Inc. Oct. 12, 1998, La Jolla California, United States, Oct. 12, 1998, 1 pg.
US Non Final Office Action, dated Apr. 14, 2015, U.S. Appl. No. 13/608,475, "Human Amniotic Membrane Lyophilized Grafts," filed Sep. 10, 2012, 11 pgs.
Allen, Claire L. et al., "Augmented Dried Versus Cryopreseverd Amniotic Membrane as an Ocular Surface Dressing", PLOS One, Oct. 2013, 15 pgs, vol. 8, Issue 10, e78441:1-15.
Baradaran-Rafii, Alireza et al., "Amniotic Membrane Transplantation", Iran Journal Ophthalmic Research, 2007, p. 58-75, vol. 2, No. 1.
Burgos, Hugo et al., "Lyophilized Human Amniotic Membranes Used in Reconstruction of the Ear", Journal of the Royal Society of Medicine, May 1983, p. 433, vol. 76.
Deocaris, Chester C. et al., "Radiolytic Damage of Freeze-Dried Human Amniotic Membrane", Phillippine Journal of Science, Jun. 2005, p. 45-50.
Ganatra, M.A., "Amniotic Membrane in Surgery", JPMA (Journal of Pakistan Medical Association) Jan. 2003, vol. 53, No. 1.
Gruss, Joseph S. et al., "Human Amniotic Membrane: a Versatile Wound Dressing", CMA Journal, May 20, 1978, p. 1237-1254, vol. 118.
Hanft, Jason R. et al., "Are Tissue Replacements Cost Effective", Jul. 2003, p. 1-6, vol. 16, Issue 7.
Medicis Pharmaceutical Corp., "First and Only Hyaluronic Acid Dermal Filler Approved for Lips", Photo Release—FDC Approves Lip Indication for Medicis' Restylane(R), Press Release, Oct. 11, 2011, p. 1-5, Available at: http://www.globenewswire.com/newsroom/prs/?pkgid=10827.
Mohammadi, Ali A. et al., "How Does Human Amniotic Membrane Help Major Burn Patients Who Need Skin Grafting: New Experi (Continued)

*Primary Examiner* — Bin Shen
(74) *Attorney, Agent, or Firm* — Louis H. Iselin; Iselin Law, PLLC

(57) ABSTRACT

Described herein are methods of preparing human amniotic membrane tissue grafts derived from the placenta. The grafts are composed of three layers as seen in the amniotic membrane in utero. These grafts are processed using physiologic solutions, lyophilized and terminal sterilized (via gamma irradiation in a frozen state) that thereby preserves the graft in such a manner as to retain the naturally occurring biological properties of the amniotic membrane and offer a sterile graft for transplantation. By dehydration via lyophilization and terminal sterilization in a frozen state, the graft has the advantage of storage at ambient temperatures for prolonged periods of time prior to transplantation.

15 Claims, 2 Drawing Sheets

(56) References Cited

OTHER PUBLICATIONS ences", Skin Grafts—Indictions, Applications and Current Research, Aug. 2011, p. 265-276, Available from: http://www.intechopen.com/books/skin-grafts-indications-applications-and-current-research/how-does-humanamniotic-membrane-help-major-burn-patients-who-need-skin-grafting-new-experiences.
Niknejad, Hassan et al., "Properties of the Amniotic Membrane for Potential use in tissue engineering", European Cells and Materials, vol. 15, 2008, pp. 88-99, Department of Pharmacology & Neuroscience Research Center, Tehran Iran.
Novartis "APLIGRAF", APLIGRAF Brochure, Feb. 2002, p. 1-17.
Petter-Puchner, A et al., "Human Vital Amniotic Membrane Reduces Adhesions to a Polypropylene Mesh and Suture Fixation in Experimental IPOM Repair in Rats", SAGES 2010, Poster Session P088, 12th World Congress of Endoscopic Surgery, Apr. 14-17, 2010, Society of American Gastrointestinal and Endoscopic Surgeons, Landover, MD., Apr. 2010, 1 pg.
Rodriguez-Ares, M T. et al., "Effects of Lyophilization on Human-Amniotic Membrane", ACTA Ophthalmologica, 2009, p. 396-403, vol. 87.
Tseng, C. G. Scheffer et al., "How Does Amniotic Membrane Work?", The Ocular Surface, Jul. 2004, p. 177-187, vol. 2, No. 3.
Sekiyama, Eiichi et al., "Novel Sutureless Transplantation of bioadhesive-coated, Freeze-Dried Amniotic Membrane for Ocular Surface Reconstruction", Investigative Ophthalmology & Visual Science, vol. 48, No. 4, Apr. 2007, pp. 1528-1534.
Sharma, Sabbash C. et al., "Amniotic Membrane is an Effective Burn Dressing Material", Japanese Journal of Surgery, 1985, pp. 140-143, vol. 15, No. 2.
Simons, M P. et al., "European Hernia Society guidelines on the treatment of inguinal hernia in adult patients", Hernia. Aug. 2009;13(4): p. 343-403.
Subrahmanyam, M., "Amniotic Membrane as a Cover for Microskin Grafts", British Journal of Plastic Surgery, May 23, 1995, p. 477-478, vol. 48.

\* cited by examiner

Figure 2

| | | |
|---|---|---|
| ▓▓▓ | = Epithelium Layer | |
| ≡≡≡ | = Basement Membrane Layer | |
| ███ | = Compact Layer | Stroma |
| ▧▧▧ | = Fibroblast Layer | |
| ∥∥∥ | = Intermediate (spongy) Layer | |

METHODS OF PREPARING LYOPHILIZED HUMAN TISSUES

PRIOR RELATED APPLICATIONS

U.S. patent application Ser. No. 13/608,475.

CROSS-REFERENCE TO RELATED APPLICATIONS

The present application is a Continuation of U.S. patent application Ser. No. 13/608,475, now abandoned, filed on Sep. 10, 2012, which is hereby incorporated herein in its entirety.

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL

U.S. patent application Ser. No. 13/608,475.

BACKGROUND OF THE INVENTION

Human amniotic membrane derived from the placenta has been used for nearly 100 years as a transplantable biomaterial for the surgical reconstruction of various tissues in the human body. Such a membrane has been utilized widely in the management of ocular surface disorders; utilized as a biological dressing or graft for skin (burns, skin wounds, skin ulcers); utilized to prevent tissue adhesion in surgical procedures of the spine, abdomen and pelvis; utilized as a wrap for tendon and nerve repair procedures; and utilized as a graft for dental/oral procedures. Normally, such a membrane has is either dehydrated or cryopreserved prior to storage until ready for surgical transplantation.

The placental tissue, from which the amniotic membrane is derived, is harvested after birth or after elective Cesarean section surgery. At full term of gestation, the fetal membranes of the placenta are comprised of two principal layers: (1) the outer chorion layer which is in contact with maternal cells and forms the outer aspect of the sac, and (2) the inner amniotic membrane layer which contains large amounts of collagen and is bathed by amniotic fluid contained within the sac. The amniotic membrane is a thin, translucent, elastic tissue which forms the innermost layer of the amniotic sac and the placenta. Histologically, the amniotic membrane is comprised of 3 layers (FIG. 2): an epithelial monolayer, a basement membrane and stroma. The stroma can be further subdivided into a compact layer, a fibroblast layer containing a loose network of fibroblasts, and a spongy layer.

There are storage challenges with the amniotic membrane in the cryopreserved forms as this requires refrigeration or freezing to maintain these tissue grafts. The dried forms of the amniotic membrane has a storage advantage however, the methods of drying/dehydration involve the use of heat, chemicals and sometimes the removal of the epithelial layer which renders an altered histologic profile and contributes to the destruction or reduction of the naturally occurring biological properties of the amniotic membrane as seen in nature. Described herein are amniotic membranes which are dehydrated via a lyophilized (freeze dried) method without using heat or chemicals to hereby better preserve the naturally occurring biological properties of the amniotic membrane seen in nature. Such grafts, when properly prepared, can be stored at ambient temperatures for prolonged periods of time until ready for transplantation while maintaining the histologic and biological properties seen in utero.

Amnion membrane as a tissue graft provides a natural biological barrier, a matrix for cell migration and proliferation, and naturally occurring growth factors and other biological components that contribute to healing at the site of transplantation. Such a membrane when transplanted has the added benefit of the absence of immune rejection due to the lack of most of the major histocompatibility (HLA) antigens and viable cells.

BRIEF SUMMARY OF THE INVENTION

Described herein are methods of preparing tissues, specifically human tissue grafts derived from the placenta comprised of the amniotic membrane, which is processed using physiologic solutions, lyophilization and terminal sterilization (via gamma irradiation in a frozen state) that thereby preserves the graft in such a manner as to retain the naturally occurring biological properties of the amniotic membrane and offer a sterile graft for transplantation. By dehydration via lyophilization and terminal sterilization, the graft has the advantage of storage at ambient temperatures for prolonged periods of time prior to transplantation. The advantage of this invention is that it solves the problem existing for the cryopreserved grafts, namely, the need for refrigeration or frozen storage of the graft in a wet state. This invention also solves the problem existing for the heat/chemical dried grafts, namely, the deprived biological properties remaining in a graft that has been dehydrated using heat and chemicals and/or the removal of the epithelium layer. The advantages of the invention will be realized by practice of the aspects of the description and claims subsequently described. It is to be understood that both the foregoing general description and the following detailed description are illustrative and exemplary only and are not restrictive.

BRIEF DESCRIPTION OF THE DRAWINGS

The accompanying drawings, which are incorporated in and constitute a part of this specification, illustrate the following aspects.

FIG. 2 is an exemplary histological representation sketch of the layers of the tissue grafts.

DETAILED DESCRIPTION OF THE INVENTION

Figure 1:
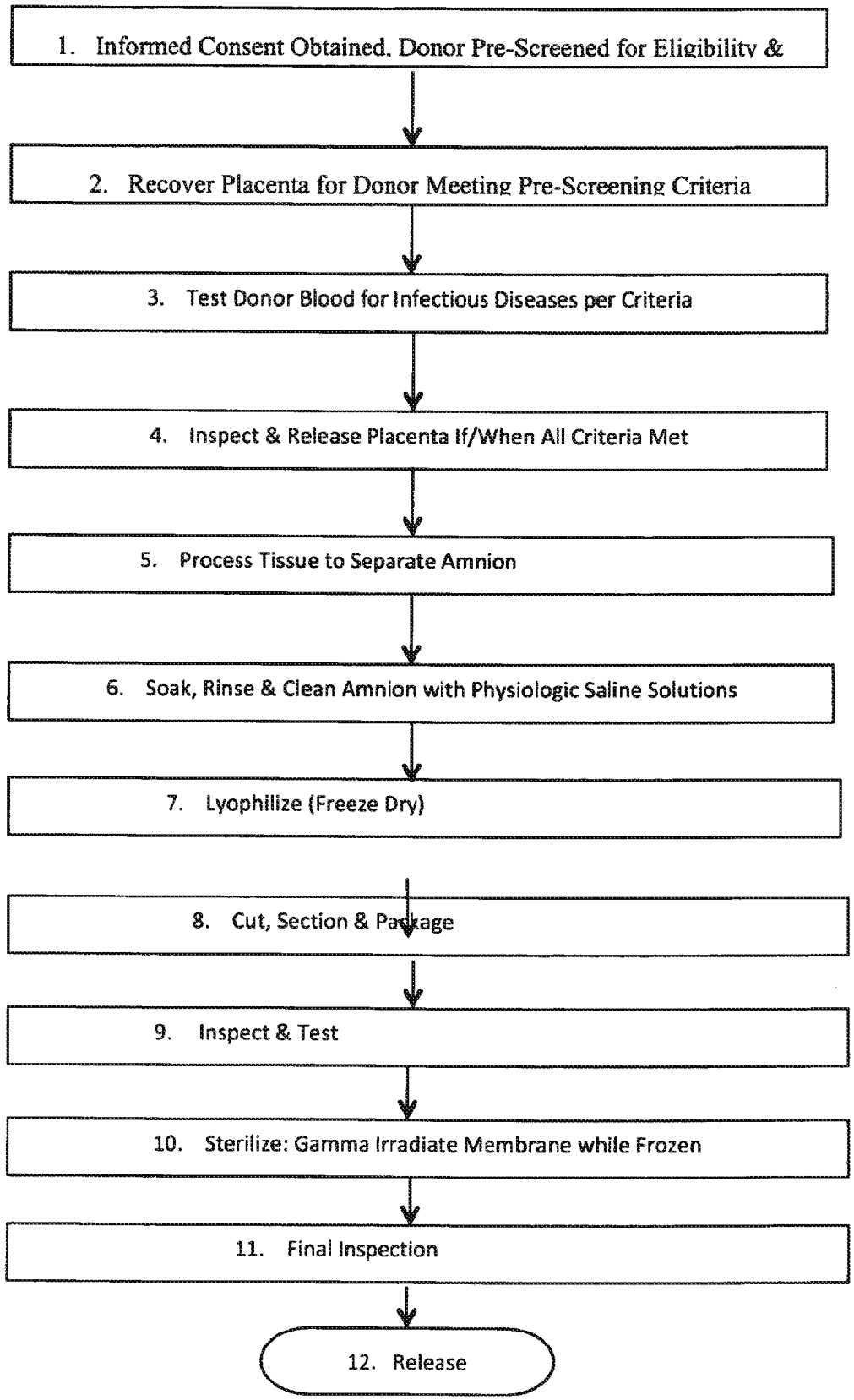
FIG. 1 is a process overview flowchart for the recovery and manufacture of the tissue grafts described herein.

First it is to be understood that the aspects of the methods to be described are not limited to specific compounds, exact methods described or uses as such may vary. FIG. 1 depicts a process overview flowchart for the recovery and manufacture of the tissue grafts described herein.

Step 1: Informed Consent Obtained, Donor Pre-Screened for Eligibility and Suitability Initially, the potential female donor is approached and written informed consent is obtained following standard industry practices and the guidelines set forth by AATB. The potential donor must fully understand the donation process and give their informed consent to the process and to the testing of their blood for diseases that may affect the suitability of their placenta tissues for use.

After written consent is obtained, the donor is pre-screened for eligibility and suitability to donate her placenta at delivery. Screening involves assessment for risk factors to communicable diseases as specified in the Food and Drug Administration's (FDA) Donor Eligibility Guidance documents and regulations for Good Tissue Practices (GTP) for human tissue products intended for human transplantation. Additionally, standards put forth by the American Association of Tissue Banks (AATB) are also used as guidelines for donor eligibility criteria. After initial pre-screening information is reviewed, a determination is made as to whether the donor is eligible to donate and plans are made for the recovery of the placenta upon delivery.

Step 2: Recover Placenta for Donor Meeting Pre-Screening Criteria

The recovery of the placenta takes place in a hospital or birthing center where it is collected during a live Cesarean section or vaginal delivery birth. The placenta is recovered by the operating room or delivery personnel and placed in sterile designated containers, labeled with distinct donor identification information. The packaged placenta is then either shipped on wet or dry ice to the processing facility or it is temporarily stored in a freezer until it can be shipped to the processing facility.

Step 3: Test Donor Blood for Infectious Diseases Per Criteria

Blood samples are drawn from the donor within 7 days before or after delivery and sent to a CLIA accredited contract laboratory to be tested for communicable diseases such as hepatitis, AIDS, Syphilis, and West Nile Virus using FDA licensed test kits, where appropriate. The specific list of tests for these communicable diseases that are performed are per the current FDA Donor Eligibility and GTP requirements and per AATB's standards.

Step 4: Inspect & Release Placenta if/when all Criteria Met

The placenta container is inspected at the processing facility upon receipt. All donor medical history charts are compiled and reviewed to include completed behavioral, sexual, medical, clinical, and health questionnaires, results of serology testing for communicable diseases, pre-natal history and medical records and hospital/birthing center delivery records. Once all donor criteria are met, the placenta is released for processing.

Step 5: Process Tissue to Separate Amnion

The placenta is thawed (if previously frozen) in a controlled environment and all processing methods are conducted in a controlled environment following FDA's GTP and AATB standards. Equipment and the facilities used are cleaned and decontaminated and all major processing steps are documented following industry practice, FDA regulations and AATB standards. Critical processes are validated per FDA requirements. Work areas are draped prior to usage and supplies and instruments are either sterile or clean with known manufacturing methods to control incoming bioburden.

The placenta is inspected for abnormalities and pre-processing samples are taken to determine the baseline Bioburden. Placentas passing inspection are further processed by separating the amnion layers from both sides of the placenta from the chorion layers and the rest of the placenta. The isolated amnion layers in the form of continuous sheets of tissue are then further processed.

Step 6: Soak, Rinse & Clean Amnion with Physiologic Saline Solutions

The isolated amnion sheets are further processed by briefly soaking for up to 1 hour at room temperature in a physiologic saline solution such as Earle's Balanced Salt Solution (1×) or Hank's Balanced Salt Solution (1×) with periodic gentle mixing to disassociate blood from the amnion. During this time, multiple subsequent rinses with Earle's or Hank's, as needed, may be performed to further remove the blood during the soak time. During or upon completion of the soak and rinse processes, any remaining blood clots or blood on the surface of the amnion may be manually removed. The resultant amnion sheets are now ready for lyophilization.

Step 7: Lyophilize (Freeze Dry)

The amnion sheets are spread out on parchment paper with the stromal side face down, placed on lyophilization trays, placed in sealed lyophilization bags and lyophilized at approximately −40 to −45° C. for 20-48 hours using standard lyophilization methods until moisture is removed and desired drying is achieved. Freeze dry time may vary depending on the thickness of the tissue and the size of the amnion sheets.

Step 8: Cut, Section & Package

The freeze dried (lyophilized) amnion sheets are sectioned into desired sizes (e.g. 4 cm×4 cm, 4 cm×6 cm, etc.) using any sharp cutting device (e.g. a scalpel, a device similar to a pizza cutter, etc.), packaged and sealed (e.g. heat sealed, vacuum sealed, etc.).

Step 9: Inspect & Test

Routine quality inspections of each unit are performed to ensure that manufacturing criteria are met in the areas of size, appearance, package integrity, etc. Standard residual moisture tests may be performed on random units to ensure consistency of the freeze drying process.

Step 10: Sterilize—Gamma Irradiate Amniotic Membrane while Frozen

The lyophilized amnion products are shipped to a contract sterilizer to be gamma irradiated by a validated method to achieve a Sterility Assurance Level (SAL) of $10^{-6}$. The gamma irradiation is performed on dry ice with product in the frozen state to circumvent damage to the tissue. Sterilized product is returned to the possession of the processor for a final inspection.

Step 11: Final Inspection

Sterilized product returned from the contract sterilizer is inspected at by the processing facility for final release. Inspection will include package integrity inspection and final labeling inspection, to name a few. Units passing inspection are released for storage, distribution and subsequent transplantation.

What is claimed is:

1. A method of preparing a tissue to be a biological dressing or a tissue graft, said method comprising, in listed order:
   processing and cleaning, consisting of using only a physiologic saline solution and physical manipulation, an amniotic membrane maintaining the following layers in the following order:
   a) an epithelium layer;
   b) a basement membrane layer; and
   c) a stroma layer comprising an upper compact layer, a middle fibroblast layer, and a lower spongy layer;

freezing and dehydrating while lyophilizing, without heat or chemicals, the amniotic membrane after said cleaning to create a frozen, dehydrated amniotic membrane; and in a frozen state, sterilizing the frozen, dehydrated amniotic membrane using gamma irradiation.

2. The method of claim 1, further comprising:
separating the amniotic membrane from a placental tissue before said cleaning.

3. The method of claim 2, further comprising:
obtaining human placental tissue from which to extract the amniotic membrane.

4. The method of claim 1, further comprising:
before said sterilizing, packaging the amniotic membrane.

5. The method of claim 4, further comprising:
storing the tissue at room temperature after said sterilizing.

6. The method of claim 5, further comprising:
wrapping or replacing a damaged tissue with the tissue.

7. The method of claim 6, wherein said wrapping or replacing the damaged tissue with the tissue comprises wrapping or replacing a damaged tendon, damaged oral tissue, or damaged gastrointestinal mucosa, damaged epidermal tissue with the tissue.

8. The method of claim 4, further comprising:
sectioning the amniotic membrane before packaging.

9. The method of claim 1, further comprising:
wrapping or replacing a damaged tissue with the amniotic membrane after said sterilizing.

10. The method of claim 9, wherein said wrapping or replacing comprises wrapping or replacing a damaged tendon, damaged oral tissue, damaged gastrointestinal mucosa, or damaged epidermal tissue.

11. A method of preparing a tissue to be a biological dressing or a tissue graft, said method comprising:
step for processing an amniotic membrane consisting of using only physiologic saline solution and physical manipulation;
step for cleaning, consisting of using only physiologic saline solution and physical manipulation, an amniotic membrane maintaining the following layers in the following order:
a) an epithelium layer;
b) a basement membrane layer; and
c) a stroma layer comprising an upper compact layer, a middle fibroblast layer, and a lower spongy layer;
step for freezing and dehydrating while lyophilizing, without heat or chemicals, the amniotic membrane to create a frozen, dehydrated amniotic membrane, after said step for cleaning; and
step for sterilizing the frozen, dehydrated amniotic membrane in a frozen state using gamma irradiation, after said step for freezing and dehydrating while lyophilizing.

12. The method of claim 11, further comprising:
step for obtaining human placental tissue from which to extract the amniotic membrane.

13. The method of claim 11, further comprising:
before said step for sterilizing, step for packaging the amniotic membrane.

14. The method of claim 13, further comprising:
step for storing the tissue at room temperature after said step for sterilizing.

15. The method of claim 13, further comprising:
step for sectioning the amniotic membrane before said step for packaging.

* * * * *